US006967337B1

(12) United States Patent
Fonowich

(10) Patent No.: US 6,967,337 B1
(45) Date of Patent: Nov. 22, 2005

(54) TOOTHBRUSH CLEANING ASSEMBLY

(76) Inventor: Andrew Fonowich, 84 Marion St., Carteret, NJ (US) 07008

( * ) Notice: Subject to any disclaimer, the term of this patent is extended or adjusted under 35 U.S.C. 154(b) by 16 days.

(21) Appl. No.: 10/739,978

(22) Filed: Dec. 19, 2003

(51) Int. Cl.[7] .......................... H01J 37/20; G01J 1/00; B65D 83/10
(52) U.S. Cl. .................... 250/455.11; 250/491.1; 211/126.1
(58) Field of Search ............... 250/455.11, 491.1; 211/126.1; 312/206; 206/361, 368

(56) References Cited

U.S. PATENT DOCUMENTS

| 2,587,131 | A | * | 2/1952 | Ficken | .................. 250/455.11 |
| 4,806,770 | A | | 2/1989 | Hylton et al. | |
| 4,888,487 | A | | 12/1989 | Ritter | |
| 4,973,847 | A | * | 11/1990 | Lackey et al. | .......... 250/455.11 |
| 5,023,460 | A | * | 6/1991 | Foster et al. | ............ 250/455.11 |
| 5,029,252 | A | * | 7/1991 | Ameseder | .............. 250/455.11 |
| 5,126,572 | A | | 6/1992 | Chu | |
| D396,768 | S | | 8/1998 | Drake | |
| 5,799,910 | A | * | 9/1998 | Dexter | ......................... 248/109 |
| 2004/0211683 | A1 | * | 10/2004 | Barham et al. | ........... 206/209.1 |

FOREIGN PATENT DOCUMENTS

| DE | 19614779 | * | 4/1997 |
| JP | 2000325442 | * | 11/2000 |

* cited by examiner

*Primary Examiner*—John R. Lee
*Assistant Examiner*—Kalimah Fernandez

(57) ABSTRACT

A toothbrush cleaning assembly includes a housing having a bottom wall and a peripheral wall that is attached to and extends upwardly from the bottom wall. An upper edge of the peripheral wall defines an opening extending into the housing. A cover is selectively positioned over the opening for selectively closing the opening. An ultra violet light emitter is mounted in the housing. A power supply is electrically coupled to the light emitter. A panel has a top side and a bottom side. The panel is removably positioned in the housing such that the bottom side abuts the bottom wall. The top side has a plurality of wells extending therein. Toothbrushes may be removably positioned in the wells and the light emitter turned on such that the toothbrushes are exposed to ultraviolet light.

8 Claims, 4 Drawing Sheets

TOOTHBRUSH CLEANING ASSEMBLY

BACKGROUND OF THE INVENTION

1. Field of the Invention

The present invention relates to toothbrush sterilizing devices and more particularly pertains to a new toothbrush sterilizing device for killing germs on toothbrushes by the use of ultraviolet light.

2. Description of the Prior Art

The use of toothbrush sterilizing devices is known in the prior art. U.S. Pat. No. 4,973,847 describes a device for utilizing light to sanitize toothbrushes. Another type of toothbrush sterilizing device is U.S. Pat. No. 5,023,460 which also utilizes light for killing germs found on toothbrushes. While these devices fulfill their respective, particular objectives and requirements, the need remains for a device that offers a simpler construction for more efficient use. Such efficiency promotes the use of device which will prevent the spread of germs across toothbrushes.

SUMMARY OF THE INVENTION

The present invention meets the needs presented above by providing a panel for having wells therein for receiving the bottom end of a toothbrush for easy insertion of the toothbrushes into a housing containing the panel.

Another object of the present invention is to provide a new toothbrush sterilizing device that includes sleeves which may be selectively positioned in the wells for altering a diameter of the wells and thereby allowing the wells to receive varying sized toothbrushes.

Still another object of the present invention is to provide a new toothbrush sterilizing device that allows removal of the panel so that the panel may be cleaned as required.

To this end, the present invention generally comprises a housing having a bottom wall and a peripheral wall that is attached to and extends upwardly from the bottom wall. An upper edge of the peripheral wall defines an opening extending into the housing. A cover is selectively positioned over the opening for selectively closing the opening. An ultra violet light emitter is mounted in the housing. A power supply is electrically coupled to the light emitter. A panel has a top side and a bottom side. The panel is removably positioned in the housing such that the bottom side abuts the bottom wall. The top side has a plurality of wells extending therein. Toothbrushes may be removably positioned in the wells and the light emitter turned on such that the toothbrushes are exposed to ultraviolet light.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
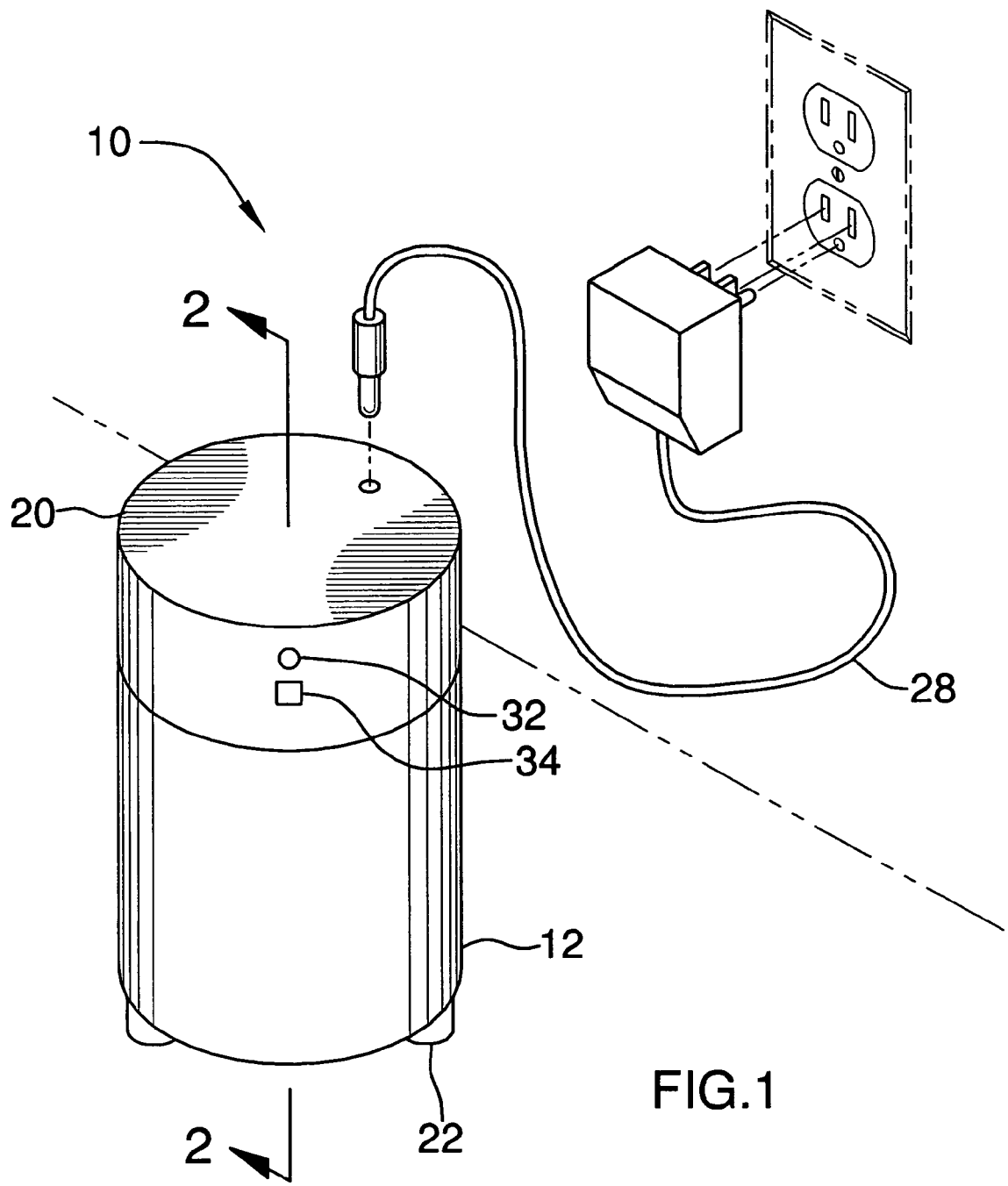
FIG. 1 is a schematic perspective view of a toothbrush cleaning assembly according to the present invention.
Figure 2:
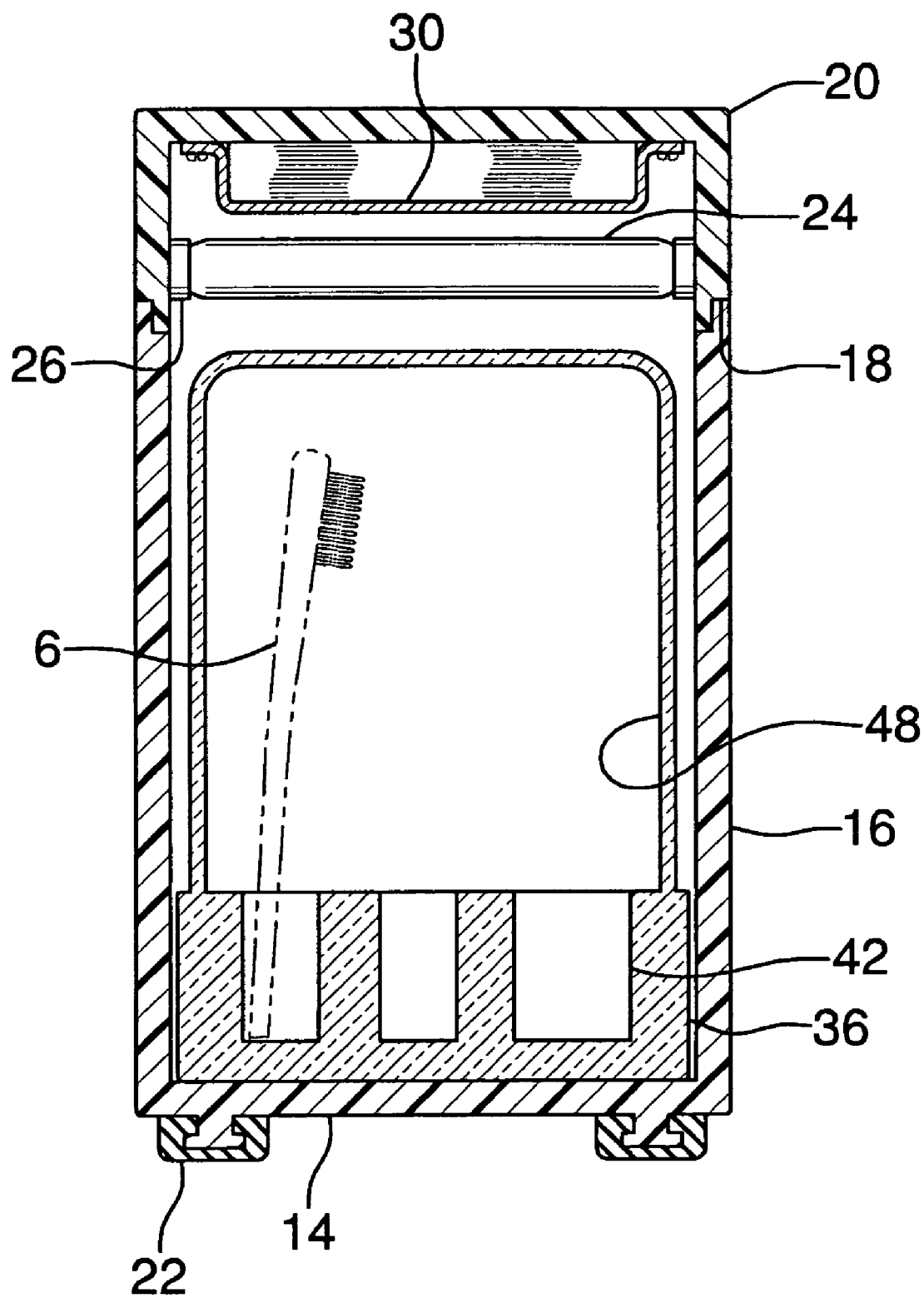
FIG. 2 is a schematic cross-sectional view taken along line 2—2 of FIG. 1 of the present invention.
Figure 3:
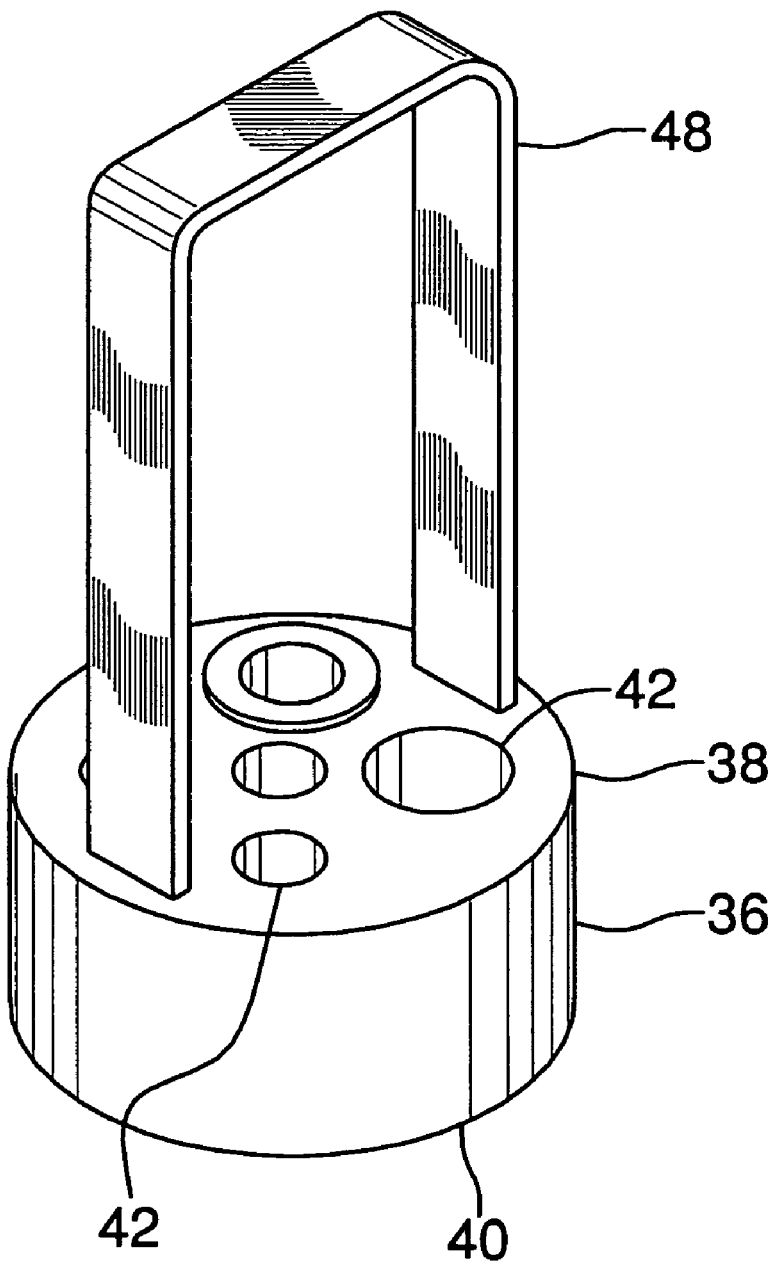
FIG. 3 is a schematic perspective view of the panel of the present invention.
Figure 4:
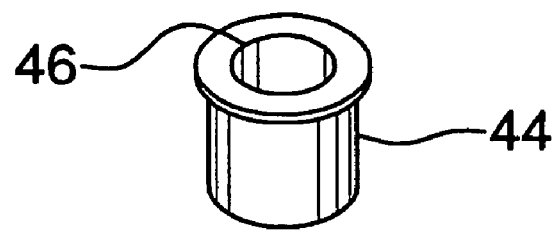
FIG. 4 is a schematic perspective view of a sleeve of the present invention.
Figure 5:
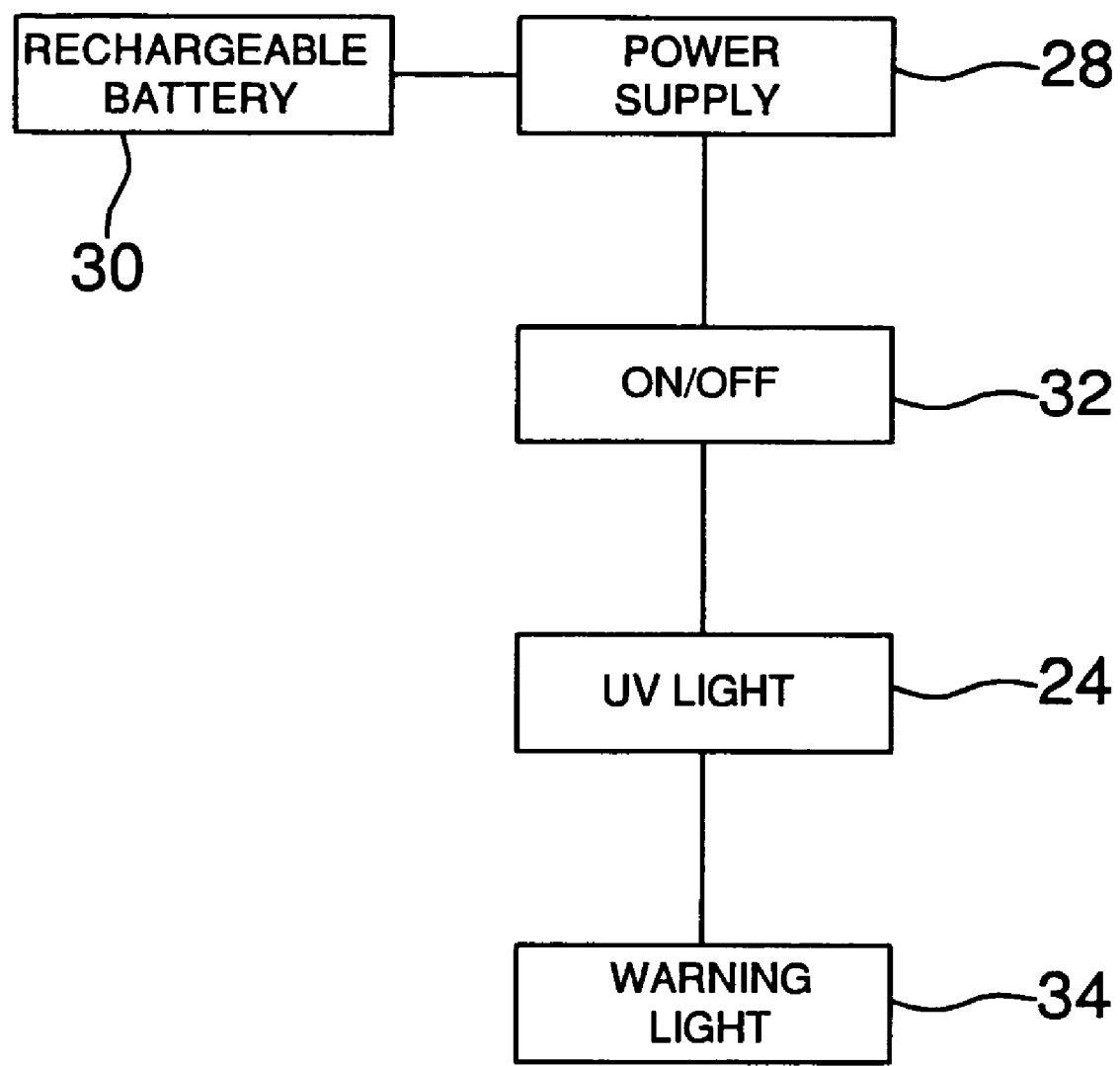
FIG. 5 is an electronic schematic view of the present invention of the present invention.

With reference now to the drawings, and in particular to FIGS. 1 through 5 thereof, a new toothbrush sterilizing device embodying the principles and concepts of the present invention and generally designated by the reference numeral 10 will be described.

As best illustrated in FIGS. 1 through 5, the toothbrush cleaning assembly 10 generally comprises a housing 12 having a bottom wall 14 and a peripheral wall 16 that is attached to and extends upwardly from the bottom wall 14. An upper edge 18 of the peripheral wall 16 defines an opening extending into the housing 12. A cover 20 is selectively positioned over the opening for selectively closing the opening. The cover 20 may be hingedly coupled to the peripheral wall 16 or the cover 20 and peripheral wall 16 may include mating flanges for snapping the cover 20 onto the peripheral wall 16. Each of a plurality of feet 22 is preferably attached to the bottom wall 14.

An ultra violet light emitter 24 is mounted in the housing 12. The light emitter 24 is preferably mounted on the cover 20 and is positioned such that light emitted by the light emitter 24 is directed toward the bottom wall 14. The light emitter 24 is preferably mounted in a conventional light socket 26 so that it may be replaced as needed. A power supply 28 is electrically coupled to the light emitter 24. The power supply 28 preferably includes a conventional power cord and also preferably includes a rechargeable battery 30 so that the assembly may be used without a power socket. An actuator 32 is operationally coupled to the power supply 28 for selectively turning the light emitter 24 on or off. The actuator 32 is preferably a switch mounted on the housing 12. The actuator 32 may include a timer for turning on the light emitter for a specified amount of time. Additionally, it is preferred that a usage warning light 34 is mounted on the housing 12 and electrically coupled to the power supply 28 for warning a user of the assembly 10 that the light emitter 24 is turned on.

A panel 36 has a top side 38 and a bottom side 40. The panel 36 is removably positioned in the housing 12 such that the bottom side 40 abuts the bottom wall 14. The top side 38 has a plurality of wells 42 extending therein. The panel 36 preferably comprises a substantially transparent material which is ideally a plastic material. Optionally, a plurality of sleeves 44 may be provided. Each of the sleeves 44 has an open upper end 46. The sleeves 44 are each removably positioned into one of the wells 42 for selectively reducing a diameter of the wells 42. The sleeves 44 may be constructed of either a plastic or an elastomeric material. The wells 42 and sleeves 44 each preferably have a tubular shape. By reducing the size of the sleeves 44, the wells 42 can be adapted for receiving different sized toothbrushes 6.

Also, it is preferred that wells 42 of varying sizes are formed in the panel 36. A handle 48 is attached to and extends upwardly from the panel 36. The handle 48 preferably comprises a substantially transparent material.

In use, the ends of one or more toothbrushes 6 may be removably positioned in the wells 42 so that the heads of the toothbrushes 6 are positioned near the light emitter 24. The light emitter 24 is turned on so that the toothbrushes 6 are exposed to ultraviolet light.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A toothbrush disinfecting assembly comprising:
   a housing having a bottom wall and a peripheral wall being attached to and extending upwardly from said bottom wall, an upper edge of said peripheral wall defining an opening extending into said housing, a cover being selectively positioned over said opening for selectively closing said opening;
   an ultra violet light emitter being mounted in said housing;
   a power supply being electrically coupled to said light emitter;
   a panel having a top side and a bottom side, said panel being removably positioned in said housing such that said bottom side abuts said bottom wall, said top side having a plurality of wells extending therein;
   a plurality of sleeves, each of said sleeves having an open upper end, each of said sleeves being removably positioned into one of said wells for selectively reducing a diameter of said wells; and
   wherein toothbrushes may be removably positioned in said wells and said light emitter turned on such that the toothbrushes are exposed to ultraviolet light.

2. The assembly of claim 1, wherein said light emitter is mounted on said cover.

3. The assembly of claim 1, further including an actuator being operationally coupled to said power supply for selectively turning said light emitter on or off.

4. The assembly of claim 1, wherein said panel comprises a substantially transparent material.

5. The assembly of claim 1, further including a handle being attached to and extending upwardly from said panel.

6. The assembly of claim 5, wherein said handle comprises a substantially transparent material.

7. The assembly of claim 6, wherein said panel comprises a substantially transparent material.

8. A toothbrush disinfecting assembly comprising:
   a housing having a bottom wall and a peripheral wall being attached to and extending upwardly from said bottom wall, an upper edge of said peripheral wall defining an opening extending into said housing, a cover being selectively positioned over said opening for selectively closing said opening;
   an ultra violet light emitter being mounted in said housing, said light emitter being mounted on said cover;
   a power supply being electrically coupled to said light emitter;
   an actuator being operationally coupled to said power supply for selectively turning said light emitter on or off;
   a panel having a top side and a bottom side, said panel being removably positioned in said housing such that said bottom side abuts said bottom wall, said top side having a plurality of wells extending therein, said panel comprising a substantially transparent material;
   a plurality of sleeves, each of said sleeves having an open upper end, each of said sleeves being removably positioned into one of said wells for selectively reducing a diameter of said wells;
   a handle being attached to and extending upwardly from said panel, said handle comprising a substantially transparent material; and wherein toothbrushes may be removably positioned in said wells and said light emitter turned on such that the toothbrushes are exposed to ultraviolet light.

* * * * *